US00RE40014E

(19) United States
(12) Reissued Patent
Edwards

(10) Patent Number: US RE40,014 E
(45) Date of Reissued Patent: *Jan. 22, 2008

(54) METHOD FOR PRESENTING HIGH LEVEL INTERPRETATIONS OF EYE TRACKING DATA CORRELATED TO SAVED DISPLAY IMAGES

(75) Inventor: Gregory T Edwards, Roseville, CA (US)

(73) Assignee: The Board of Trustees of the Leland Stanford Junior University, Palo Alto, CA (US)

( * ) Notice: This patent is subject to a terminal disclaimer.

(21) Appl. No.: 10/227,065

(22) Filed: Aug. 22, 2002

Related U.S. Patent Documents

Reissue of:
(64) Patent No.: 6,106,119
Issued: Aug. 22, 2000
Appl. No.: 09/437,735
Filed: Nov. 9, 1999

U.S. Applications:
(63) Continuation of application No. 09/173,849, filed on Oct. 16, 1998, now abandoned.
(60) Provisional application No. 60/107,873, filed on Nov. 9, 1998.

(51) Int. Cl.
*A61B 3/14* (2006.01)

(52) U.S. Cl. ..... 351/209

(58) Field of Classification Search ..... 351/200, 351/203, 209, 246; 600/544, 545; 359/630; 345/156–158.8
See application file for complete search history.

(56) References Cited

U.S. PATENT DOCUMENTS 5,564,433 A * 10/1996 Thornton ..... 600/544
5,886,683 A * 3/1999 Tognazzini et al. ..... 715/700
5,982,555 A * 11/1999 Melville et al. ..... 359/630

* cited by examiner

*Primary Examiner*—George Manuel
(74) *Attorney, Agent, or Firm*—Blakely, Sokoloff, Taylor & Zafman

(57) ABSTRACT

A software program stores during a recording session eye-tracking data and all other communication device activities of a test person that self-controlled confronts her/himself with display scenarios or virtual pages. The display scenarios are stored simultaneously either:

1. after a predetermined elapse time interval,
2. after recognizing a raised attention level of the test person,
3. after a positive result of a scrolling detection process.

In a consecutive processing cycle, the software program utilizes an eye interpretation engine to derive high level information and visualizes them superimposed on the correlated image scenarios.

49 Claims, 4 Drawing Sheets

METHOD FOR PRESENTING HIGH LEVEL INTERPRETATIONS OF EYE TRACKING DATA CORRELATED TO SAVED DISPLAY IMAGES

Matter enclosed in heavy brackets [ ] appears in the original patent but forms no part of this reissue specification; matter printed in italics indicates the additions made by reissue.

CROSS-REFERENCE TO RELATED APPLICATION

This application is in part a continuation of U.S. application Ser. No. 09/173,849 filed Oct. 16, 1998, now abandoned and the provisional U.S. application Ser. No. 60/107,873 filed Nov. 9, 1998.

FIELD OF INVENTION

The present invention relates generally to the field of eye tracking and methods for processing eye tracking data. In particular, the invention relates to a system and method for presenting high level interpretations of eye tracking data correlated to saved display images.

BACKGROUND OF INVENTION

A computer user typically retrieves processed information on the visual level by watching a screen or a display device. In recent years the graphical complexity of displayed information has significantly increased allowing the user to observe simultaneously a multitude of images, text, graphics, interaction areas, animations and videos in a single displayed image. This diversity is preferably utilized in web pages, which have become a significant communication medium through the gaining global influence of the internet.

Web pages and other visual compositions or scenarios designed for computer assisted display intend to exceed the viewable area of screens and display devices. As a result, scrolling features are added to virtually move the viewable area over a larger display scenario.

Visual compositions are created for many purposes and have to fulfill expected functions like for instance informing, advertising or entertaining. The multitude of available design elements and their possible combinations make it necessary to analyze the display scenarios for their quality and efficiency. A common technique to provide the necessary information for this analysis is to track eye movements.

A number of eye tracking devices are available that track the eye movement and other elementary eye behaviors. Their precision is such that dot like target points corresponding to a center of an observers gazing area can be allocated on the display device. The eye tracker generates a continuous stream of spatio-temporal data representative of eye gaze positions, at sequential moments in time. Analysis of this raw data typically reveals a series of eye fixations separated by sudden jumps between fixations, called saccades.

The human eye recognizes larger objects as for instance a virtual page by scanning it in a number of fixations. The scanning rate ranges typically between 2 and 5 fixations per second. The time an observer needs to view a virtual page and consequently the number of fixations depend mainly on the number of details and the complexity of information and text in the virtual page or the display scenario.

A plot of all fixations that are tracked and correlated to a displayed virtual page typically shows arhythmically placed dots with highly differing densities. An informative survey of the current state of the art in the eyetracking field is given in Jacob, R. J. K., "Eye tracking in advanced interface design", in W. Barfield and T. Furness (eds.), Advanced interface design and virtual environments, Oxford University Press, Oxford, 1995. In this article, Jacob describes techniques for recognizing fixations and saccades from the raw eye tracker data.

An interpretation engine developed by the current inventor identifies elementary features of eye tracker data, such as fixations, saccades, and smooth pursuit motion. The interpretation engine also recognizes the elementary features of a plurality of eye-movement patterns, i.e., specific spatio-temporal patterns of fixations, saccades, and/or other elementary features derived from eye tracker data. Each eye-movement pattern is recognized by comparing the elementary features with a predetermined eye-movement pattern template. A given eye-movement pattern is recognized if the features satisfy a set of criteria associated with the template for that eye-movement pattern. The method further includes the step of recognizing from the eye-movement patterns a plurality of eye-behavior patterns corresponding to the mental states of the observer.

The eye interpretation engine provides numerous pieces of information about eye behavior patterns and mental states that need to be graphically presented together with the correlated screen, display scenario, or a virtual page. The current invention addresses this need.

Eye tracking analysis programs need to refer or reconstruct the original display scenario in order to assign the stored eye tracking data correctly. Two general approaches are known in the prior art to address this need:

1. Video-based eye-tracking output: A videotape is taken during a recording session where the test person is confronted with the display event or virtual pages that need to be analyzed. The videotape is usually taken from the test person's view by using a head-mounted scene camera that records the display events simultaneously with an eye-tracking camera that records eye movements. Typical eye-analysis software programs analyze in a consecutive processing operation the raw eye-tracking data and superimpose an indicator on the video corresponding to the test person's gaze location over the image taken by the scene camera. As a result, a videotape shows the display events during the recording session with a superimposed indicator. The researcher can then watch the videotape in order to see the objects the test person looked at during the recording session. The problem with a video movie of the display events with a dancing indicator is that the visual analysis process is very time consuming such that eye-tracking studies are typically constrained to testing sessions lasting only a few minutes. For demographically or statistically representative studies with a number of test persons this technique is highly unpractical.

2. Reconstruction of the original environment: A second approach to associate the eye-movement data with a displayed scenario is to reconstruct the display event of the recording session and display it with superimposed graphical vocabulary that is associated with the eye tracking data. Reconstructing the display event is only possible for simple static scenarios. Virtual pages like web pages that involve scrolling, or other window based application scenarios cannot be reconstructed with the correct timing and the recorded eye-tracking data cannot be associated properly. Web pages have in general a highly unpredictable dynamic behavior, which is caused by their use of kinetic elements like videos or animation. Their unpredictability is also caused by down loading discrepancies dependent on the quality of the modem connection and web page contents.

Therefore, there exists a need for a method to capture a dynamic display event in real time correlation to recorded eye-tracking data. The current invention addresses this need.

To view web pages a user has to operate other communication devices such as a keyboard or a mouse to perform zooming or scrolling of the virtual page. For window based application scenarios mouse and keyboard are used to open, close and manipulate windows, pop up menus and to perform other functions as they are known for computer operation. In order to associate the display events in real time with the correlated eye-tracking data it is necessary simultaneously record all communication device interactions of the test person during the recording session. The current invention addresses this need.

U.S. Pat. No. 5,831,594 discloses a method and apparatus for eyetrack derived backtrack to assist a computer user to find the last gaze position prior to an interruption of the eye contact. The invention scrolls a virtual page and highlights the last entity of a virtual page that had the last fixation immediately prior to the interruption. The invention does not interpret eye tracking data, it only takes one piece of fixation information to trigger the highlighting function, which operates to assign a virtual mark assigned to the last entity. The invention does not present any qualitative information or comparative interpretations.

U.S. Pat. No. 5,898,423 discloses a method and apparatus for eyetrack-driven captioning, whereby a singular mental state of interest is determined to trigger a simultaneous presentation of additional information. The invention does not present any qualitative information or comparative interpretation.

The Web page www.eyetracking.com describes a method to allocate areas of interests of an observer by either superimposing fixations and saccades onto the analyzed display scenario (ADP) or by opposing the ADP to a corresponding spectral colored area graph. The density of the superimposed fixations i.e. the colors of the area graph are thought to represent attention levels. The described method does not present any qualitative information or comparative interpretations and can be applied only to reproducible display events consisting of a number of static scenarios.

The Web page www.smi.de describes a method to allocate areas of interests of an observer by superimposing graphical symbols onto the ADP. The graphical symbols are assigned to fixations and are scaled correspondingly to the density or duration of the fixations. The individual graphical symbols are connected with each other to visualize the fixation chronology. The described method does not present any qualitative information or comparative interpretation about the utilized eye-tracking data and can be applied only to reproducible display events consisting of a number of static scenarios.

OBJECTS AND ADVANTAGES

It is a primary object of the present invention to record and store simultaneously the visual experience of a test person, all of his or her communication device activity and the display event so that the test person's interactions and visual experiences can be reconstructed and correlated to the corresponding individual display scenarios, which define the display event.

It is a further object of the present invention to reconstruct display scenarios resulting from scrolled virtual pages.

It is an object of the present invention to reconstruct display scenarios resulting from any software program application that utilizes window and/or pop up menu functions.

It is an object of the present invention to assign a graphical valuation vocabulary to high level interpretations like eye behaviors and/or basic mental states that are processed from the recorded visual experience by the use of the eye interpretation engine.

It is a further object of the present invention to enable the recorded visual and communication data to be viewed simultaneously or in alternating succession with the graphical valuation vocabulary in unlimited configurations, including viewing one or more snapshots of the test person's activity at the same time.

It is an object of the invention to provide a method to store the display scenario without a priori available display event information.

It is an object of the present invention to provide a method to record a coordinate information of a viewable display area correlatingly to recorded eye tracking data.

It is an object of the invention to provide a method to record a coordinate information of a virtual image correlatingly to recorded eye tracking data.

SUMMARY OF THE INVENTION

The invention refers to a software program stored on a storing device of a computer that operates during a recording session and a processing cycle. During the recording session a test person wears an eyetracker that is connected to the display driving computer as it is known to those skilled in the arts. During the recording session, the test person controls the display events and confronts himself in a real life manner with the display scenarios and/or virtual pages that need to be analyzed. Eye-gazing and eye-movements of the test person are time stamped recorded and stored within the computer as are all activities of the keyboard and the mouse.

Dependent on the time related appearing characteristic of the analyzed scenarios or virtual pages three different modes of storing the displayed scenarios can be individually or in combination employed. The selection can be performed by the user. In case of a pre-definable appearing rate of the display scenario like for instance during a presentation, the storing can be performed at a predetermined repeating rate, which correlates preferably to the frame rate used for computer displayed videos, animations or flics. In case of virtual pages that pre-knowingly exceed the viewable area of the screen, the display can be stored immediately following a scrolling operation performed by the test person. To recognize a scrolling operation, typically without interacting with the scenario generating application, the software program continuously performs a three-step scrolling detection process. In a first step, all windows displayed within the scenario are detected. In the consecutive second step, each window information is compared with scrolling window pattern to find scroll bars in the scenario. After allocating an scroll bar a final third step is initiated in which the location of the scroll window within the scroll bar is continuously observed. Each change of the location coordinates indicates a successful scrolling operation and triggers a storing of the new display scenario.

There exists also a third case, in which the scenarios have contents alterations that are highly unstable and unpredictable. This third case happens for instance during real life analyses of web pages with unpredictable download durations and download discrepancies of individual page segments like for instance pictures. To cover this third case, the software program provides a setup, in which the recorded eye tracking data is simultaneously processed and compared with a predetermined eye-behavior pattern to recognize increased attention levels. This comparison is enabled by utilizing the eye interpretation engine as it is disclosed in Gregory T. Edwards' "Method for Inferring Mental states from Eye Movements", to which this application is a continuation in part.

Every time an increased attention level is recognized, a significant web page event like for instance the play of a video or the finished download of a picture is interpreted and the storing of the display scenario is initiated. Storing operations are time stamped such that they can be correlated to the corresponding eye-tracking data during a consecutive processing cycle.

The recording session can be repeated with a number of test persons for demographically or statistically valid analysis results.

In a consecutive processing cycle the software program utilizes the eye interpretation engine to process the recorded eye tracking data and to convert it into high level interpretations that reveal informations about eye behaviors and basic mental states of the test person(s). The eye interpretation engine performs a three level processing. In the first level elementary features like fixations and saccades are identified, in the second level eye-movement patterns are identified, and in the third level eye-behavior patterns and basic mental states are determined as mentioned above.

Even though the goal of the analysis are the three level interpretations, the software program is able to assign a graphical valuation vocabulary (GVV) to results from all three level and is able to present them superimposed on the correlated display scenarios. In case of scrolled virtual pages that exceed the display size, the individual captured page segments are recombined and can be zoomed together with the superimposed GVV to fit into the display area.

The software program also assigns a GVV to statistic and demographic informations. The GVV can be preset within the software program or defined by the user. Qualitative and quantitative informations can be represented in scaled proportion of the individual elements of the GVV as it is known to those skilled in the art.

The final analysis of the results can be presented in various timing modes, from real time replay to user controlled step by step display of the stored display scenarios.

The software program derives all image event information from the operating system independently of the image scenario generating application.

To provide accurate processing results, the software optionally stores additional coordinate information of the display scenario that are real time correlated to the recorded eye-tracking data. The software references the coordinate information either to the viewable display area or to a scrollably displayed virtual page as it is known to those skilled in the art.

DETAILED DESCRIPTION

Although the following detailed description contains many specifics for the purposes of illustration, anyone of ordinary skill in the art will appreciate that many variations and alterations to the following details are within the scope of the invention. Accordingly, the following preferred embodiment of the invention is set forth without any loss of generality to, and without imposing limitations upon, the claimed invention.

Figure 1:
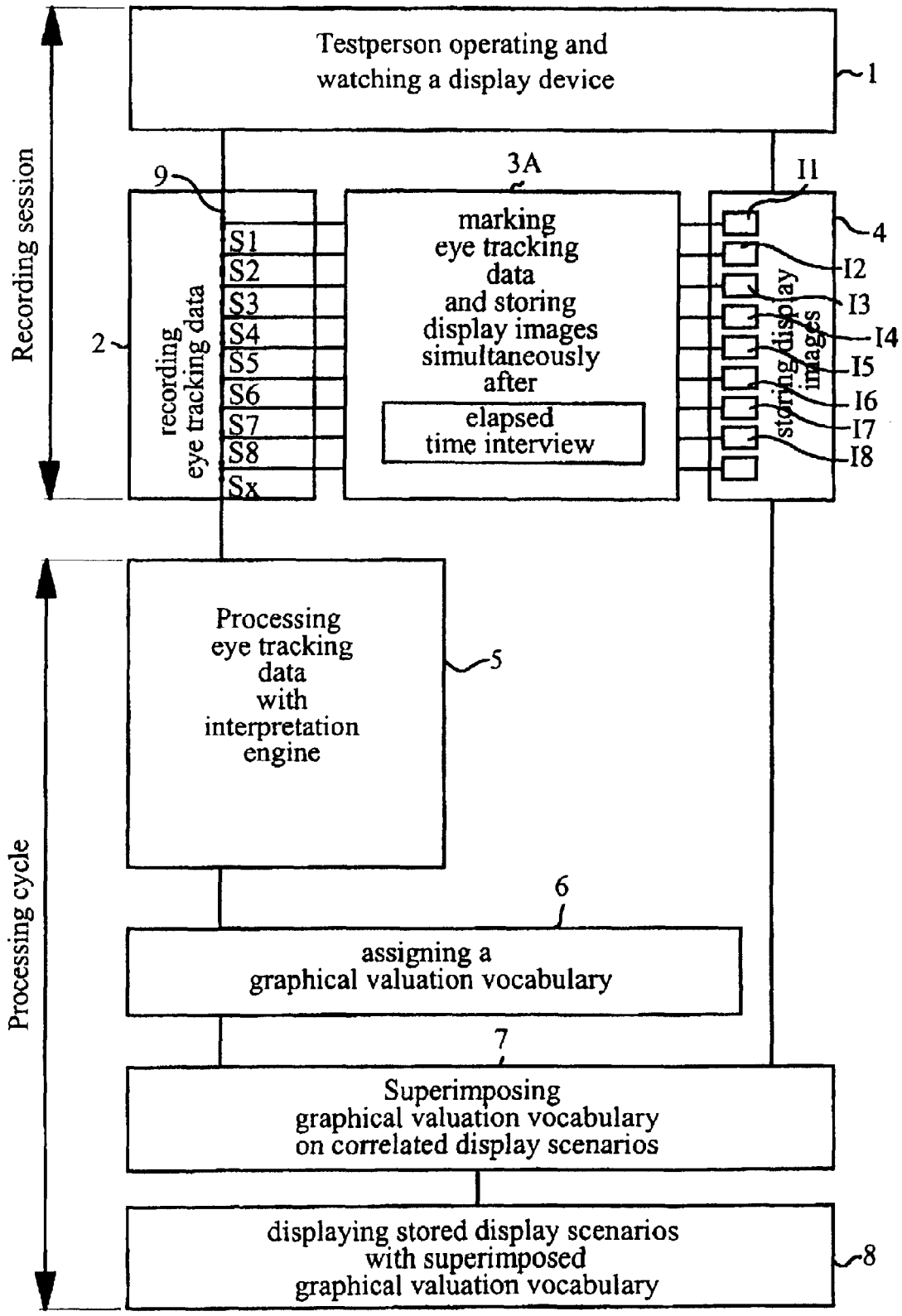
FIG. 1 shows an event diagram visualizing the operation of the invention with a recording setup for image scenarios according to elapsed time intervals.

FIG. 1 shows a diagram representing the principal events performed by the invention respectively the software program. The upper half of the diagram shows the main events that characterize the invention during a recording session.

The first event box 1 indicates a test person being placed in front of a screen or other display device and wearing an eyetracker as it is known to those skilled in the art. The eyetracker is connected via an interface to the computer as well as other communication devices like for instance a keyboard or a mouse. The test person itself controls the display event and confronts him/herself with display scenarios in a real life manner. The software program controls the storing process by preferably writing the eye tracking data together with information about communication device activities into a data bank on a hard drive. The test person initiates and manipulates the display scenarios and virtual pages according to the test procedure. The software program allows the test person to scroll intuitively virtual pages with boundaries that exceed the size of the display device or a scrolling area within the displayed scenario. Display scenarios are stored as snapshots according to a number of setup options of the software.

The second event box 2 visualizes this storing process of the eye-tracking data 9, which is typically a continues flow of angular eye movements along a horizontal and vertical plane respectively eye position along x, y and z axes, sample time, pupil diameter and open eye percentage. The third primary event box 3A indicates the main processing task performed by the software program during the recording session. In the case visualized in FIG. 1 the software program accordingly initiates after each predetermined elapsed time interval the recording and storing of the scenario snapshots I1-x as it is visualized in the fourth event box 4. The software program simultaneously adds a time stamp to the continuously receiving eye-tracking data and the recorded snapshots I1-x. Hence, interval the sequences S1-x of the eye-tracking data 9 correlate to the scenario snapshots I1-x.

It is appreciated that the predetermined elapsed time intervals correspond to the frame rate of typical computer displayed videos, animations or flics. It is appreciated that anybody skilled in the art may record the eye tracking data and/or the snapshots on any other analog or digital storing device.

To obtain statistic or demographic information, the recording session is optionally repeated with a number of different test persons. The real life environment during the recording session that is provided by the functional concept of the invention reduces the setup periods for each recording session and supports real life testing that is favorable for representative analysis of virtual pages and display scenarios.

The software program provides a processing cycle that is performed after the recording session(s) is(are) completed. The fifth event box 5 indicates a first processing event performed by the software program, in which the eye tracking data is processed within the eye interpretation engine disclosed in the US application of Gregory T. Edwards for a "Method for Interring Mental States from Eye Movements", Ser. No. 09/173,849 filed Oct. 16, 1998.

The eye interpretation engine performs a three-level interpretation process. Level one processing analyzes the raw eye-tracking data to identify elementary features, typically fixations, saccades, smooth pursuit motion and blinks as they are known to those skilled in the art.

Fixations are typically defined by position, time and duration. Saccades are typically defined by magnitude, direction and velocity. Smooth pursuit motions are typically defined by the path taken by the eye and its velocity. Blinks are typically defined by their duration.

Level two processing analyzes the elementary features to identify eye-movement patterns, typically consisting of a set of several fixations and/or saccades satisfying certain predetermined criteria. A listing of typical eye-movement patterns and their criteria is shown below.

LEVEL 2 - EYE-MOVEMENT PATTERN TEMPLATES

| Pattern | Criteria |
|---|---|
| Revisit | The current fixation is within 1.2 degrees of one of the last five fixations, excluding the fixation immediately prior to the current one |
| Significant Fixation | A fixation of significantly longer duration when compared to other fixations in the same category |
| Vertical Saccade | Saccade Y displacement is more than twice saccade X displacement, and X displacement is less than 1 degree |
| Horizontal Saccade | Saccade X displacement is more than twice saccade Y displacement, and Y displacement is less than 2 degree |
| Short Saccade Run | A sequence of short saccades collectively spanning a distance of greater than 4 degrees |
| Selection Allowed | Fixation is presently contained within a region that is known to be selectable |

Level three processing, in turn, analyzes the eye-movement patterns to identify various eye-behavior patterns and subsequently various basic mental states that satisfy particular criteria. Examples of basic mental states are mental activities, intentions, states, and other forms of cognition whether conscious or unconscious. A listing of typical patterns for eye-behavior and mental states, respectively their criteria are shown below.

LEVELS 3. EYE-BEHAVIOR PATTERN TEMPLATES

| Pattern | Criteria |
|---|---|
| Best Fit Line (to the Left or Right) | A sequence of at least two horizontal saccades to the left or right. |
| Reading | Best Fit Line to Right or Short Horizontal Saccade while current state is reading |

-continued

LEVELS 3. EYE-BEHAVIOR PATTERN TEMPLATES

| Pattern | Criteria |
|---|---|
| Reading a Block | A sequence of best fit lines to the right separated by large saccades to the left, where the best fit lines are regularly spaced in a downward sequence and (typically) have similar lengths |
| Re-Reading | Reading in a previously read area |
| Scanning or Skimming | A sequence of best fit lines to the right joined by large saccades with a downward component, where the best fit lines are not regularly spaced or of equal length |
| Thinking | several long fixations, separated by short spurts of saccades |
| Spacing Out | several long fixations, separated by abort spurts of saccades, continuing over a long period of time |
| Searching | A Short Saccade Run, Multiple Large Saccades, or many saccades since the last Significant Fixation or change is user state |
| Re-acquaintance | Like searching, but with longer fixations and consistant rhythm |
| Intention to Select | "selection allowed" flag is active and searching is active and current fixation is signficant |

As it is shown above, a multitude of interpretations at different levels is derived from the comparatively low number of elementary features derived at level one of the eye interpretation engine. Level one interpretations correspond to the level of information provided in prior art visualization methods. The software program provides in addition statistic and demographic information derived from multiple recording sessions.

The sixth event box 6 visualizes the process of assigning a graphical valuation vocabulary (GVV) to the interpretations of all levels. The GVV is assigned either automatically from a software program library, which can be altered or enhanced by the user. The GVV provides elements that are scaleable in proportion to a magnitude of some interpretations like for instance thinking or the number of re-reading. Scaleable GVV are in particular used to visualize statistic and demographic information. The GVV are semitransparent and typically in different colors to assist the proportional visualization and to keep the symbol variety low.

The Seventh event box 7 visualizes the process of superimposing the GVV on the correlated display scenarios and storing the correlated results. Virtual pages with boundaries exceeding the size of the display device are welded together out of the individual snapshots. The software program provides the possibility to either scroll through the welded and reconstructed snapshot or to zoom and fit it into the viewable area of the display device. In such a case the GVV is scaled proportional.

The eighth event box 8 visualizes the process of displaying the stored correlated results. The software program provides a layer structured display technique to allow the user to distinctively view particular GVV. The layer structure is either automatically assigned to the different levels of interpretation or can be defined by the user.

The presentation of the analysis results can be controlled by the user or run in adjustable time intervals. The software program operates application independent and does not need any special information assistance whether from the operating system nor from the application that provides the display scenarios. As a result, the software program can be installed at any typical computer and enhances its feasibility as a favorable real life analysis tool.

In the near future, display devices will incorporate eye-tracker as a common feature, allowing an analysis of web pages at a test person's own personal computer. In an alternate embodiment, the independent operating software is incorporated in a web browser and/or is a self extracting attachment of a web page and thus utilizes a general availability of eyetrackers to support web page analysis with a large number of test persons.

Figure 2:
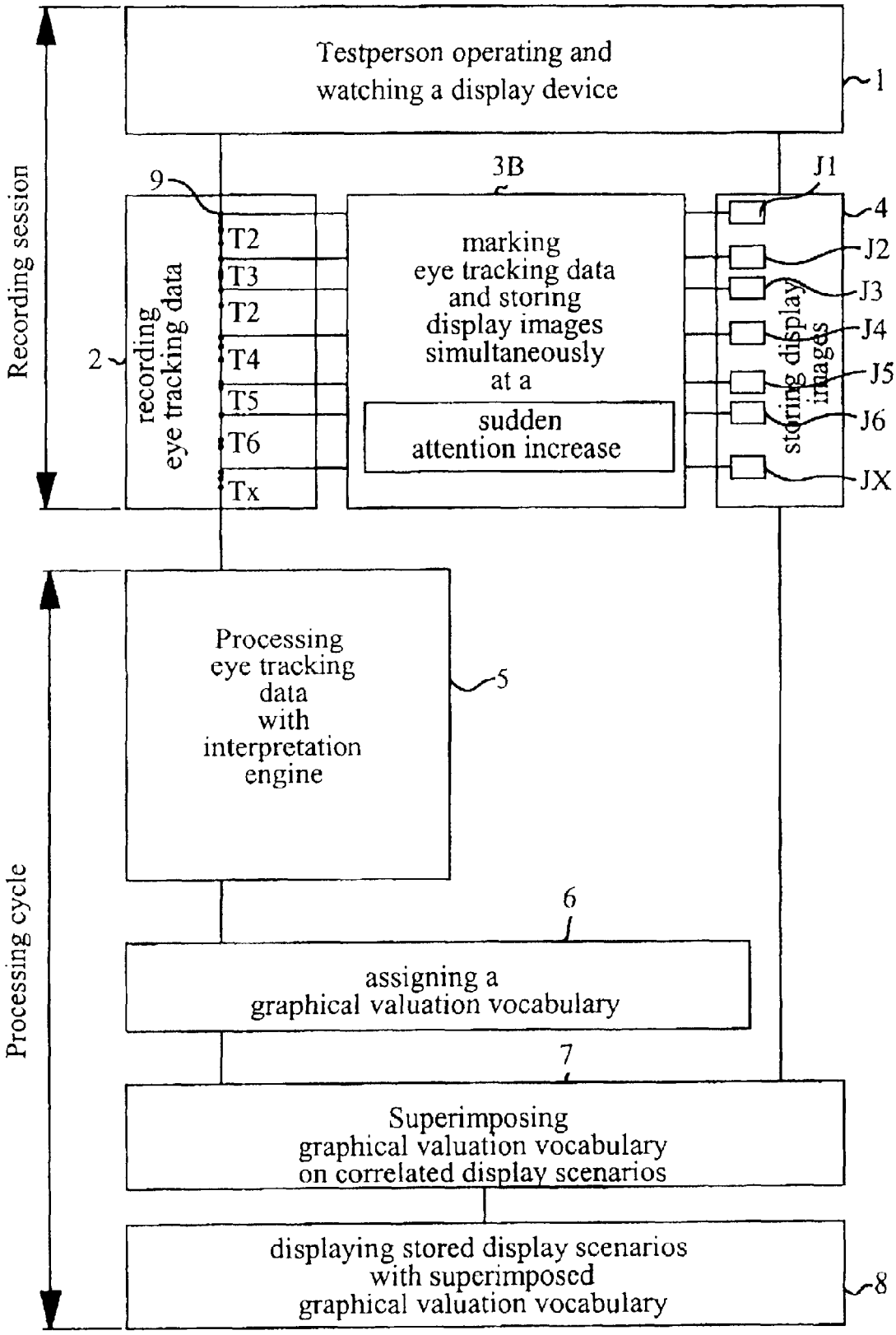
FIG. 2 shows an event diagram visualizing the operation of the invention with a recording setup for image scenarios according to a sudden attention increase.

FIG. 2 relates to the second recording option, in which snapshot is taken after a recognized sudden attention increases or a predetermined behavior pattern that is correlated to a significant moment in the display event. The contents visualized in FIG. 2 diverts from the contents described under FIG. 1 solely in the recording events described in event boxes 2, 3B and 4.

Web pages have typically a dynamic appearance, which depends mainly on their incorporation of animations and videos, but is also defined by down loading time differences of the individual web page elements. The software recognizes predetermined eye behavior patterns and mental states that indicate dynamic web page events. Every time a predetermined eye behavior pattern of the test person is recognized by the software program, a significant display event takes place or is accomplished and the recording and storing of a snapshot is initiated. A predetermined eye behavior pattern is preferably a sudden attention increase.

Hence, in the case visualized in FIG. 2 the software program accordingly initiates after each sudden attention increase the recording and storing of a scenario snapshot J1-x as it is visualized in the fourth event box 4. The software program simultaneously adds a time stamp to the continuously receiving eye-tracking data and the recorded snapshot I1-x. Thus, interval sequences T1-x of the eye-tracking data 9 correlate to a scenario snapshot J1-x.

Figure 3:
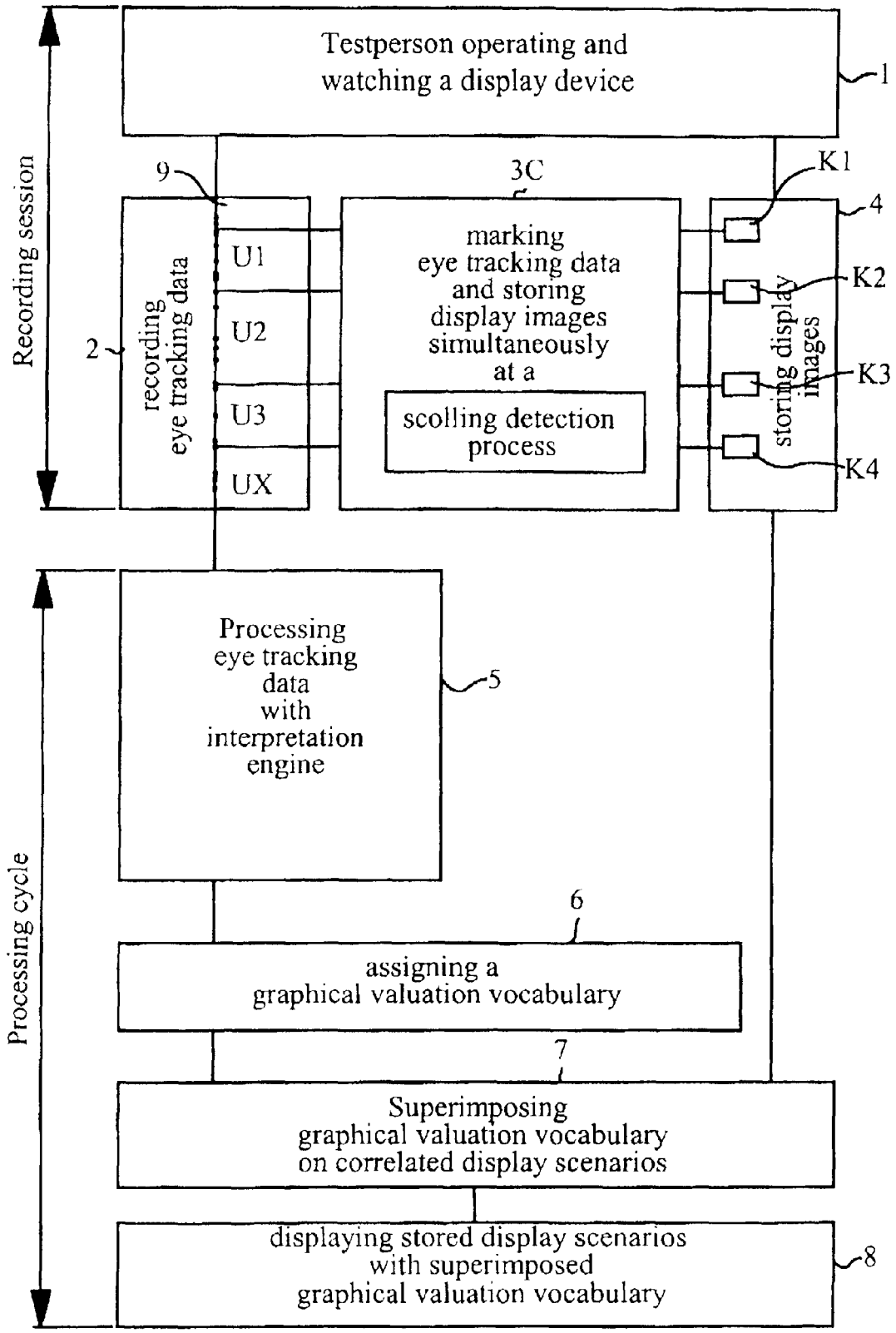
FIG. 3 shows an event diagram visualizing the operation of the invention with a recording setup for image scenarios according to a positive result of a scrolling detection process.

FIG. 3 relates to the third recording option, in which a scrolling detection process is applied. The contents visualized in FIG. 3 diverts from the contents described under FIG. 1 solely in the recording events described in event boxes 2, 3B and 4.

The size of web pages typically exceed the visible area of the display device. The viewing of exceedingly sized web pages is typically provided by the software in two forms: In a first form the whole viewable display area can be scrolled. The software welds the web page together and allows to present it together with the superimposed GVV zoomed to fit the viewable display area or in real life scale.

In a second form, the web page itself has a scrollable area, in which a larger virtual page can be scrolled and viewed. The software recognizes the larger virtual page, welds it together and allows to present it either together with the superimposed GVV zoomed to fit the viewable display area or in original scale, partially visible together with the surrounding web page.

The software differentiates in the same way between the cases where the web page is displayed within the viewable display area or within a scrollable window of the providing application. The welding and zooming functions are applied for this differentiation in same way as it is explained in the two paragraphs above. The providing application is typically a web browser.

The third tertiary event box 3C visualizes a setup condition of the software program where the storing of the display snapshots K1-x is initiated after a scrolling operation has been performed by the test person. The scrolling operation is recognized by applying a scrolling detection algorithm.

This setup option is provided to cover the case of virtual pages that exceed with their boundaries the viewable area of the display device as it is typical for web-pages. The setup option described in FIG. 3 allows to incorporate in the analyzing process of web pages the intuitive scrolling initiated by the test person, which gives significant information about the ergonomic design of the web page. The scrolling detection algorithm is preferably a three step detection algorithm. The three steps perform the following tasks:

1. all windows presented in the displayed scenario are detected;
2. each of the detected windows is compared with criteria templates to find scroll windows 14 (see FIG. 4), the scroll bar 15 (see FIG. 4) and the first and second scroll direction window 20, 21 (see FIG. 4);
3. after detecting the scroll bar 15 the location coordinates are continuously observed. In case of a location change, scrolling is detected and a snapshot is initiated.

The software captures activities of other communication devices like keyboard and mouse and utilizes it to make a snapshot. As a result, scrolling operations performed with a mouse device or dedicated scroll buttons of the keyboard are captured as well as hyper text selections for a later analysis together with correlatingly taken snapshots.

The software optionally detects scrolling with a screen scanning process, in which the pixel matrix of the display scenario is analyzed in real time for pixel patterns that are associated with scroll windows, scroll buttons or scroll bars.

In the case, visualized in FIG. 3 the software program accordingly initiates immediate after each positive result of a scrolling detection process the recording and storing of a scenario snapshot K1-x as it is visualized in the fourth event box 4. The software program simultaneously adds a time stamp to the continuously receiving eye-tracking data and the recorded snapshot K1-x. Hence, interval sequences U1-x of the eye-tracking data 9 correlate to a scenario snapshot K1-x.

The software gives the possibility to combine any of the three recording options such that a recording profile can be tailored to the available computing sources and the analyzing tasks.

To provide accurate processing results, the software optionally stores additional coordinate information of the display scenario that are real time correlated to the recorded eye-tracking data. The software references the coordinate information either to the viewable display area or to a scrollably displayed virtual page.

Figure 4:
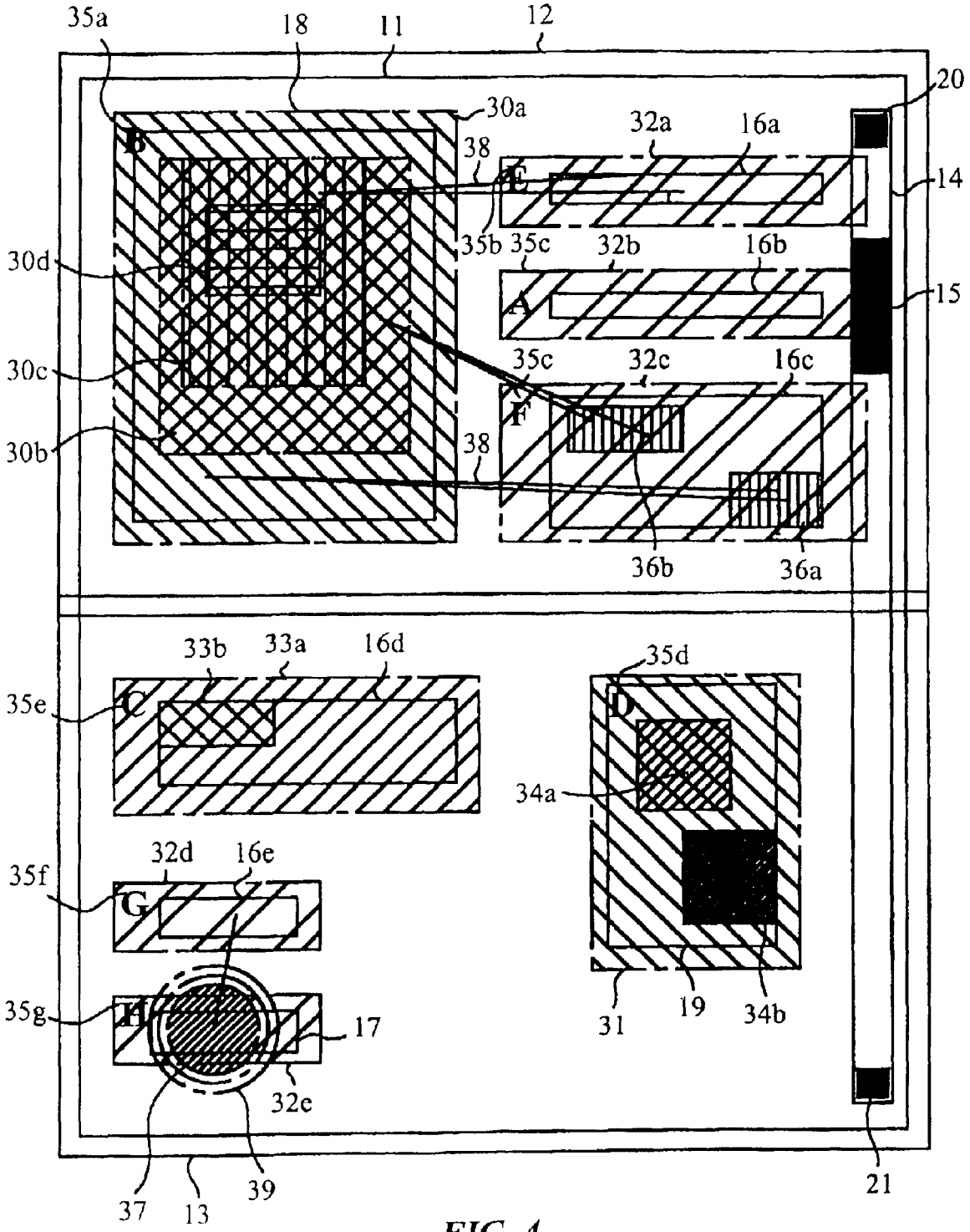
FIG. 4 shows a simplified example of a final presentation provided by the invention.

FIG. 4 shows an example of a web page with page boundaries 11. For the purpose of explanation the shown web page is welded together by an image welding function as it is known for image processing to those skilled in the art. The first and second snapshot boundaries 12 and 13 indicate the location of the display device boundaries during the storing of the snapshots.

The web page shows block text with text field boundaries 16a–e, a decision area 17 and a first and second image with first and second image boundaries 18 and 19. A scroll window 14 with the scroll bar 15 and the first and second scroll direction window 20 and 21 is positioned on the right side of the web page in this example.

In the following FIG. 4 is utilized to describe a typical example of an analyzing procedure performed with the software program. The example described in FIG. 4 is solely stated to make the advantageous features of the invention transparent without any claim for accuracy.

After the recording session has been finished with a number of test persons the processing cycle is performed by the software program as described above. The GVV is presented superimposed on the web page that has been welded together from the individual snapshots. The chosen presentation mode for FIG. 4 is a single presentation for one representative test person with superimposed level two and level three interpretation GVV.

The chronology symbols 35a–g show that the block text 16b was read first. The block reading areas 32a-e indicate, which text block was read completely. After reading the text block 16b the test person looks at the top attention area 30d of the first picture. The test person looks then on the text block 16d with the GVV 33a and 33b, which indicate a first and second re-reading. The test person looks then on the second picture, pays in general little attention, which is indicated by the second low attention area 31. The test person spends a short time thinking about a detail in the second picture, which is represented by the short thinking area 34a. A long thinking area 34b is generated by scaling the hatch width used for thinking areas 34a, 34b. This indicates that the test person must have though some more time about a second detail of the second picture before scrolling again and reading the top text block 16a, followed by the text block 16c, interrupted by glances on the first picture, which are indicated by the gross-movement indicator 38.

After glancing on the picture the test person needs to re-acquaint, which is indicated by the re-acquaintance areas 36a,b. The text bar 16c appears to be too long to be memorized by the test person between the glances of the first picture.

The test person continues to read text block 16c and looks than on decision area 17 with the intention to select, which is represented by the intention select area 37. The statistic decision indicator 39 shows with the three 25% indicator rings that 75% percent of all test persons made the decision. The statistic decision indicator belongs to one of the statistic and demographic layers that are mostly turned off in FIG. 4. The user of the software program can understand that the text block 16b dominates over 16a and 16c. The first picture also apparently dominates over text block 16c, which seems to be too long resulting in unnecessary re-acquaintance. Text block 16d needs to be rewritten. The second picture does not correlate sufficiently with the information of the text.

It is appreciated, that the GVV may be assisted or replaced in part or completely by acoustic valuation vocabulary like sounds or voices.

Accordingly, the scope of the invention should be determined by the following claims and their legal equivalents:

What is claimed is:

1. A method for presenting high level interpretations of eye tracking data correlated to stored display scenarios of a display event, said method comprising following steps:

A) storing eye tracking data and correlated display scenarios, said display scenarios being stored according to at least one of the following conditions:

1) a predetermined elapsed time interval;

2) a predetermined tracking sequence of said eye tracking data, said eye tracking data being derived and simultaneously evaluated;

3) a positive result of a scrolling detection process; and 4) a predetermined communication device activity;

B) processing said eye tracking data with an interpretation engine, whereby said eye tracking data is converted into said high level interpretations;

C) assigning a valuation vocabulary to said high level interpretations; and

D) displaying said stored display scenarios and presenting simultaneously said valuation vocabulary.

2. The method of claim 1, whereby said stored display scenarios are segments of a virtual page.

3. The method of claim 2, whereby said virtual page exceeds a viewable display area.

4. The method of claim 1, whereby said display scenario compromises a scrollable area.

5. The method of claim 4, whereby said virtual page is partially and scrollable displayed within said scroll area.

6. The method of claim 4, whereby a coordinate information is stored simultaneously and correlated to said eye-tracking data.

7. The method of claim 6, whereby said coordinate information is referenced to a viewable display area.

8. The method of claim 6, whereby said coordinate information is referenced to said virtual page.

9. The method of claim 6, whereby said coordinate information is referenced to said scrollable area.

10. The method of claim 1, whereby said predetermined tracking sequence corresponds to a predetermined attention level increase.

11. The method of claim 1, whereby said predetermined tracking sequence indicates a condition change of said display event.

12. The method of claim 1, whereby said scrolling detection process is a detection algorithm consisting of the following three steps:

A) continuously collecting data from an operation system about windows appearing during display events;

B) analyzing said windows to recognize scrolling windows; and

C) detecting location alterations of said scrolling windows.

13. The method of claim 1, whereby said scrolling detection analysis in real time a pixel matrix for pixel patterns.

14. The method of claim 13, whereby said pixel matrix is a display scenario.

15. The method of claim 13, whereby said pixel pattern relates to a scrolling initiation function.

16. The method of claim 1, whereby said high level interpretations correspond to eye behavior patterns.

17. The method of claim 1, whereby said high level interpretations correspond to basic mental states.

18. The method of claim 1, whereby said valuation vocabulary is an acoustic vocabulary.

19. The method of claim 1, whereby said valuation vocabulary is a graphical vocabulary.

20. The method of claim 19, whereby said graphical vocabulary is superimposed displayed with said stored display scenario.

21. The method of claim 19, whereby said graphical vocabulary is selectable displayed.

22. The method of claim 1, whereby said valuation vocabulary corresponds to demographic information retrieved by applying said method in a number of corresponding testing sessions.

23. The method of claim 1, whereby said valuation vocabulary corresponds to statistic information retrieved by applying said method in a number of corresponding testing sessions.

24. The method of claim 1, whereby said method is executed in form of a machine-readable code and stored on a storing device.

25. The method of claim 24, whereby said machine-readable code is part of a web browser.

26. The method of claim 24, whereby said machine-readable code is a self extracting attachment of a web page.

*27. An article storing computer-readable instructions that cause one or more hardware devices to:*

*A) store eye tracking data and correlated display scenarios, said display scenarios being stored according to at least one of the following conditions:*

*1) a predetermined elapsed time interval;*

*2) a predetermined tracking sequence of said eye tracking data, said eye tracking data being derived and simultaneously evaluated;*

*3) a positive result of a scrolling detection process; and*

*4) a predetermined communication device activity;*

*B) process said eye tracking data with an interpretation engine, whereby said eye tracking data is converted into said high level interpretations;*

*C) assign a valuation vocabulary to said high level interpretations; and*

*D) display said stored display scenarios and presenting simultaneously said valuation vocabulary.*

*28. The article of claim 27, wherein said stored display scenarios are segments of a virtual page.*

*29. The article of claim 28, wherein said virtual page exceeds a viewable display area.*

*30. The article of claim 27, wherein said display scenario comprises a scrollable area.*

*31. The article of claim 30, wherein said virtual page is partially and scrollable displayed within said scroll area.*

*32. The article of claim 30, wherein a coordinate information is stored simultaneously and correlated to said eye tracking data.*

*33. The article of claim 32, wherein said coordinate information is referenced to a viewable display area.*

*34. The article of claim 32, wherein said coordinate information is referenced to said virtual page.*

*35. The article of claim 32, wherein said coordinate information is referenced to said scrollable area.*

*36. The article of claim 27, wherein said predetermined tracking sequence corresponds to a predetermined attention level increase.*

*37. The article of claim 27, wherein said predetermined tracking sequence indicates a condition change of said display event.*

*38. The article of claim 27, wherein said scrolling detection process is a detection algorithm comprising:*

*A) continuously collecting data from an operation system about windows appearing during display events;*

*B) analyzing said windows to recognize scrolling windows; and*

*C) detecting location alterations of said scrolling windows.*

*39. The article of claim 27, wherein said scrolling detection analysis in real time a pixel matrix for pixel patterns.*

*40. The article of claim 39, wherein said pixel matrix is a display scenario.*

*41. The article of claim 39, wherein said pixel pattern relates to a scrolling initiation function.*

*42. The article of claim 27, wherein said high level interpretations correspond to eye behavior patterns.*

*43. The article of claim 27, wherein said high level interpretations correspond to basic mental states.*

*44. The article of claim 27, wherein said valuation vocabulary is an acoustic vocabulary.*

*45. The article of claim 27, wherein said valuation vocabulary is a graphical vocabulary.*

*46. The article of claim 45, wherein said graphical vocabulary is superimposed displayed with said stored display scenario.*

*47. The article of claim 45, wherein said graphical vocabulary is selectable displayed.*

*48. The article of claim 27, wherein said valuation vocabulary corresponds to demographic information retrieved by applying said method in a number of corresponding testing sessions.*

*49. The article of claim 27, wherein said valuation vocabulary corresponds to statistic information retrieved by applying said method in a number of corresponding testing sessions.*

* * * * *